US005582593A

United States Patent [19]
Hultman

[11] Patent Number: 5,582,593
[45] Date of Patent: Dec. 10, 1996

[54] AMBULATORY MEDICATION DELIVERY SYSTEM

[76] Inventor: Barry W. Hultman, 387 Brewster Rd., Bristol, Conn. 06010

[21] Appl. No.: 278,397

[22] Filed: Jul. 21, 1994

[51] Int. Cl.$^6$ .................................................. A61M 5/20
[52] U.S. Cl. .................................................................. 604/65
[58] Field of Search .................. 128/904; 604/65–67, 604/30–34, 49–53, 118, 151, 250, 251, 253

[56] References Cited

U.S. PATENT DOCUMENTS

| | | | |
|---|---|---|---|
| 4,838,275 | 6/1989 | Lee | 128/904 |
| 4,871,351 | 10/1989 | Feingold | 604/66 |
| 5,319,363 | 6/1994 | Welch et al. | 340/825.36 |
| 5,338,157 | 8/1994 | Blomquist | 417/2 |
| 5,376,070 | 12/1994 | Purvis et al. | 604/65 |
| 5,415,167 | 5/1995 | Wilk | 128/904 |

*Primary Examiner*—Manuel Mendez
*Attorney, Agent, or Firm*—McCormick, Paulding & Huber

[57] ABSTRACT

An ambulatory medication delivery system includes an ambulatory pump unit having a computer control linear motor pump for pumping predetermined volumes of fluid in accordance with a programmed delivery schedule which may be altered through communication with a remote monitoring location via a telephone data access line or via radio frequency communication. A clinician communication unit and a patient communication unit receive and send information to the ambulatory pump unit and also communicate via a telephone data modem access to the computer at a remote monitoring location at which trained health personnel can monitor a number of patient locations and alter or change medication delivery profiles as required.

26 Claims, 10 Drawing Sheets

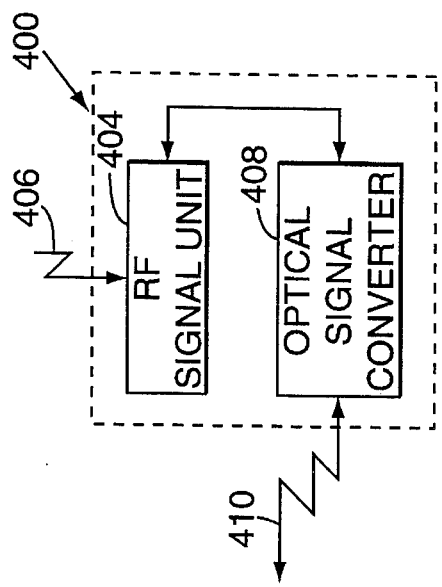
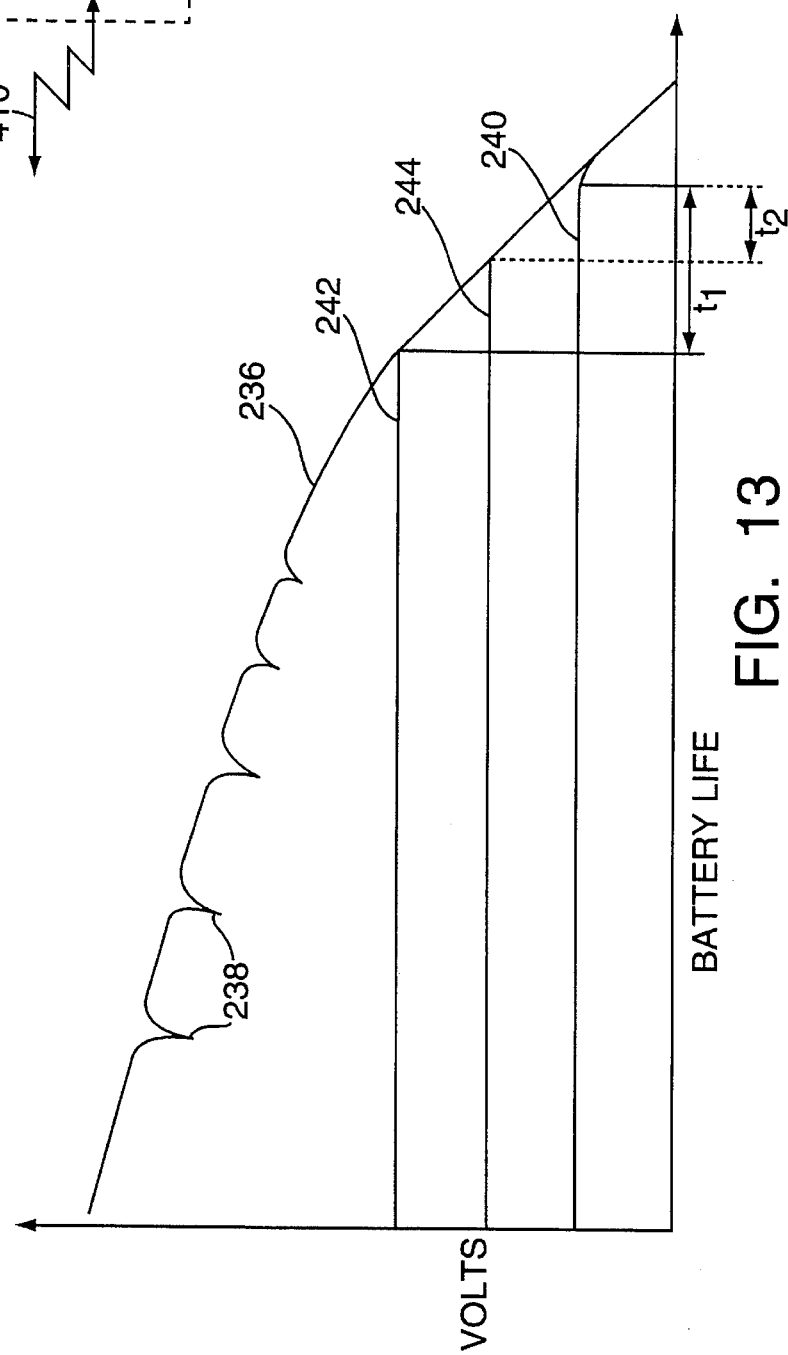

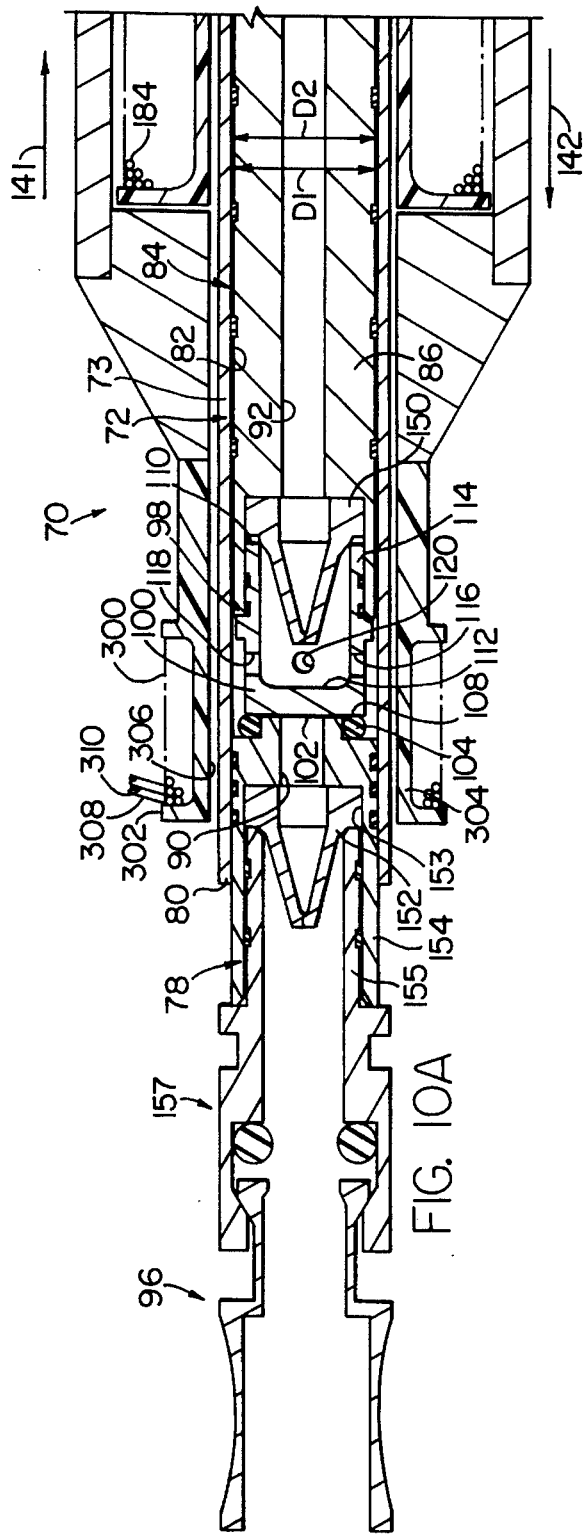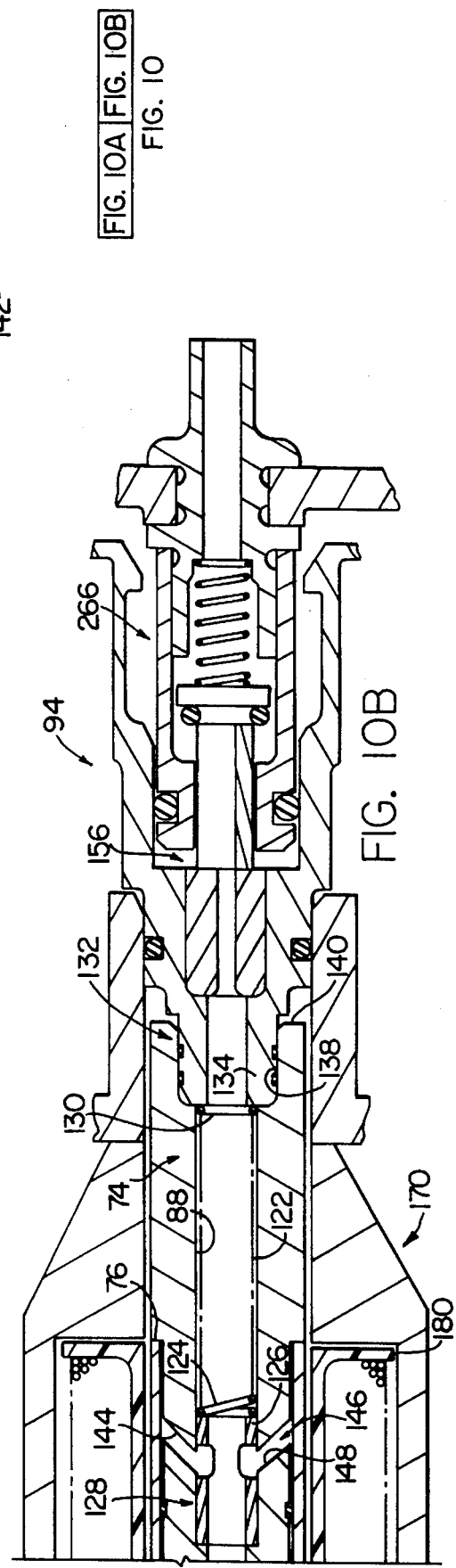

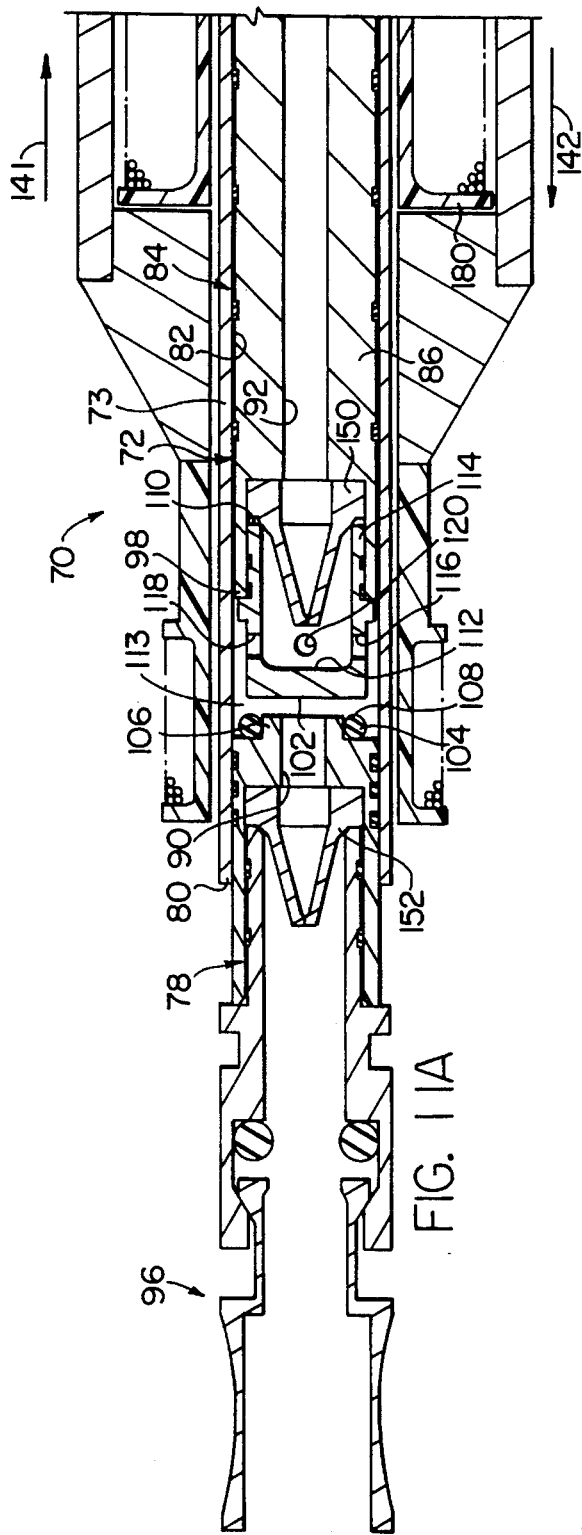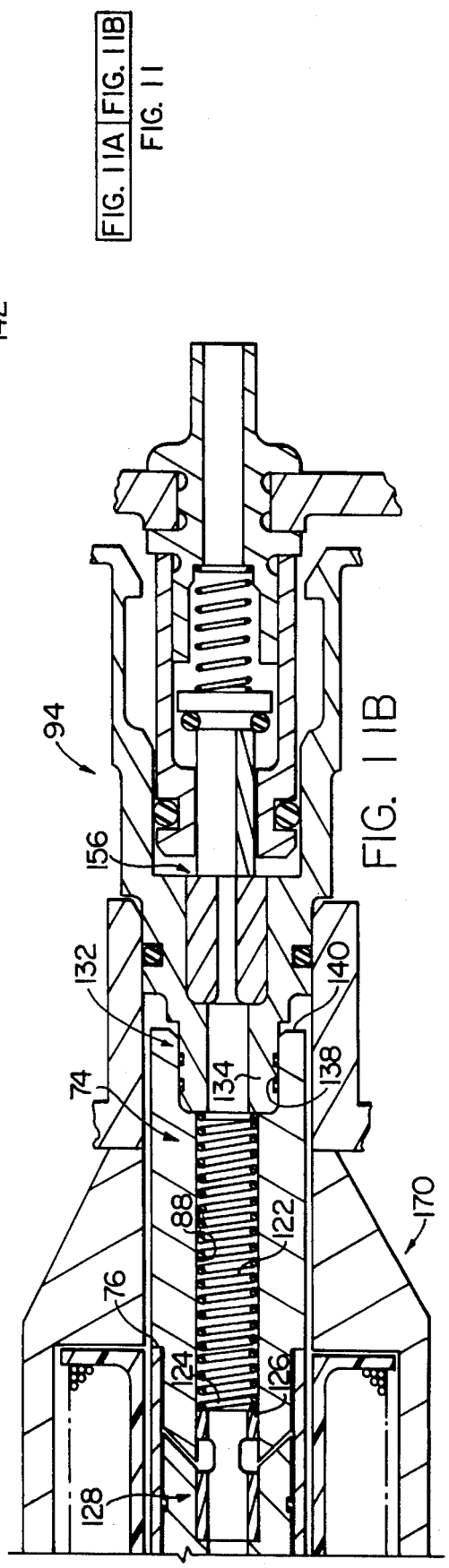

AMBULATORY MEDICATION DELIVERY SYSTEM

BACKGROUND OF THE INVENTION

The present invention relates generally to fluid medication delivery systems and associated infusion pumps and deals more particularly with a medication delivery system having a programmable, self-contained, ambulatory pump unit (APU), and communication system for retrieving information from and sending information to the APU and for communication with a computer through a communication unit which interfaces the APU to a host computer. The present invention relates further to the APU having a replaceable and disposable fluid infusion pumping system and a computer controllable micro infusion pump (MIP) for supplying desired predetermined volumes of medication or nutrients in accordance with a preprogrammed schedule.

Increased health costs, longer life spans due to improved medical diagnostics and drugs, and improved home health care and parenteral administration of medication has greatly expanded the need and demand for accurate, reliable, easy to use, low cost and virtually foolproof healthcare fluid administration systems. It is desirable that such fluid administration systems not restrict the mobility of a user or be so obtrusive as to interfere with normal day-to-day activities. It is also desirable that such fluid delivery systems be user-friendly, simple, safe-to-use, and minimize involvement of professional healthcare workers in order to be cost effective.

Drawbacks associated with known medication delivery systems in general relate to the type of pumps used to deliver the fluid, the control of the pump and lack of feedback information relating to the status of the user. All known pumps have similar problems which render them unsuitable or less than desirable for use in the safe and accurate delivery of fluid. Add-on devices and apparatus are generally required to be used with known pumps and delivery systems to assure safe operation and to cause failures to be detectable and responded to with proper reaction modes. One general class of such pumps are for example, peristaltic type pumps the operation of which is generally well known. Typically, a flexible plastic tube passes through the peristaltic pump and carries a fluid from a supply reservoir to an outlet which may be connected to a catheter for infusion into the patient. The wall of the tube is successively squeezed and released along a portion of the tube between the surface of a cam and a pressing surface in contact with the exterior surface of the tube to force the fluid within and along the interior of the tube in an amount approximately equal to the volume displaced by the cam surface in contact with the tube. The fluid is drawn into the pump from the reservoir and pressurized to flow through the outlet by the action of the rotating cam rolling over the exterior surface of the tube to infuse a recipient.

A disadvantage of known peristaltic type infusion pumps is that they are driven by a rotary motor and may fail powered, that is, with a communication path established through the pump which causes the fluid from the supply to be continuously connected to the output and therefore to the body of the recipient being infused. Such a failure mode presents a potential harm to the recipient in that an overdose or excessive medication may occur unless devices or apparatus are added to the pump to automatically preclude such action to isolate the supply of fluid to the output.

Another disadvantage of known peristaltic type infusion pumps is that it is difficult to accurately control the volumetric amount of fluid that can be incrementally delivered due to differences in the area of expansion and contraction, tolerances, wear, and pliability of the flexible tube carrying the fluid or medicant when the contact area of the cam rolls over the exterior surface of the tube.

A further limitation of known peristaltic type pumps is the inability to automatically operate the pump at predetermined pressures. Generally, peristaltic type pumps will pressurize the infused fluid to the limits of the motor capability unless additional devices are added to prevent excess fluid pressurization.

Another disadvantage generally associated with known peristaltic type pumps is their complexity, large number of parts, and relatively large size which inhibits or restricts mobility of the user and accordingly, the ambulatory infusion of fluid to a recipient is obtrusive or otherwise made not convenient.

A further disadvantage is the supply of fluid to peristaltic type pumps is generally interfaced by a complex pumping mechanism and add-on devices or apparatus which in turn may be misassembled or which may otherwise malfunction thereby increasing the chance of affecting the safe operation of the infusion unit resulting in yet further additional safety devices to be required. Consequently, in order to render the infusion unit foolproof as practical the installation of the add-on devices or apparatus greatly increases the cost and complexity, reduces reliability, increases the size of the unit and generally renders the unit unsuitable for convenient ambulatory infusion of a user.

The above and other disadvantages of known infusion pumps and fluid delivery systems are generally overcome or mitigated with the present invention which provides a computer controllable, positive displacement MIP to accurately and reliably dispense predetermined volumes of medication or nutrient fluid. The MIP and fluid delivery system of the present invention provides medication or nutrient fluid delivery in accordance with programmed infusion schedules which may be altered, modified, monitored or input from a communication unit locally or from a remote location. The fluid delivery system of the present invention is particularly suited for ambulatory infusion due to the small size of the APU and because the medication or nutrient fluid reservoir may be contained within the unit to provide direct and intimate connection to the MIP. The APU can also accommodate larger sized fluid reservoirs that cannot fit within the APU.

The APU is also suitable for use in multi-infusion applications which mix multiple medicant or nutrient fluids during programmed administration. The multi-infusion APU is also suitable for use in conjunction with preprocessing, interprocessing, and postprocessing fluids for multiple medicant profiles using simultaneous or sequential administration.

SUMMARY OF THE INVENTION

An ambulatory fluid delivery system includes in accordance with the present invention a portable infusion means or ambulatory pump unit (APU) having a reservoir for holding a supply of fluid and a computer controlled, linear motor pump for pumping predetermined volumes of the fluid in accordance with a programmed profile delivery schedule. Control means coupled to the pump via an electromagnetic coil activates the pump piston to overcome a spring preload to draw in a volume of fluid from the reservoir and then release it for infusion flow. Memory means coupled to the control means stores a program instruction set for directing the operation of the control means in accordance with a predetermined delivery schedule.

A communication unit couples the ambulatory pump unit (APU) to establish a bi-directional information transfer link therebetween to receive and transmit information from and to the APU. There are two types of communication units: a clinician communication unit (CCU) and a patient communication unit (PCU).

The CCU is a hand-held, portable, full-authority unit that includes memory means for storing information received from the APU whereby the information is uniquely identified and associated one-for-one with each one of a number of different APU's for subsequent selection and information retrieval and downloading. The CCU is a full authority unit designed for a clinician to send information to or receive information from the APU and to download and print stored data from patient locations with a resident computer. The CCU further communicates with the APU and via telephone lines through a modem access to a remote host computer for processing information.

The PCU is not a full authority unit and is designed to be used remotely via telephone lines and is intended for patient use to communicate remotely with a clinician or doctor.

In a further aspect of the invention, the communication units can communicate with the APU to provide a wireless, non-mechanical, bi-directional information transfer link, for example, by means of an infrared optical signal between them to receive and transmit information to and from the APU.

The APU can also receive information from the remote host computer via radio transmission techniques.

BRIEF DESCRIPTION OF THE DRAWINGS

Other features and advantages of the present invention will become readily apparent from the following written description and the drawings wherein:

FIG. 9 is a schematic block diagram illustrating the remote communication unit (RCU) used to convert RF frequencies to optical signals for communication with the APU;

FIG. 10 is an axial cross-sectional view of the MIP of FIG. 2 showing the pumping piston at the end of its pumping stroke and in its at-rest, "drop-tight" shutoff operative position;

FIG. 11 is an axial cross-sectional view of the MIP of FIG. 2 showing the pumping piston at the beginning of its pumping stroke;

FIG. 13 is a representative control timing waveform of the electrical current powering the main coil for the MIP;

WRITTEN DESCRIPTION OF PREFERRED EMBODIMENTS

Turning now to the drawings and considering the invention in further detail, the ambulatory medication delivery system is disclosed below in an illustrative embodiment and is made up of four main modules or component assemblies.

Ambulatory Pump Unit

Figure 1:
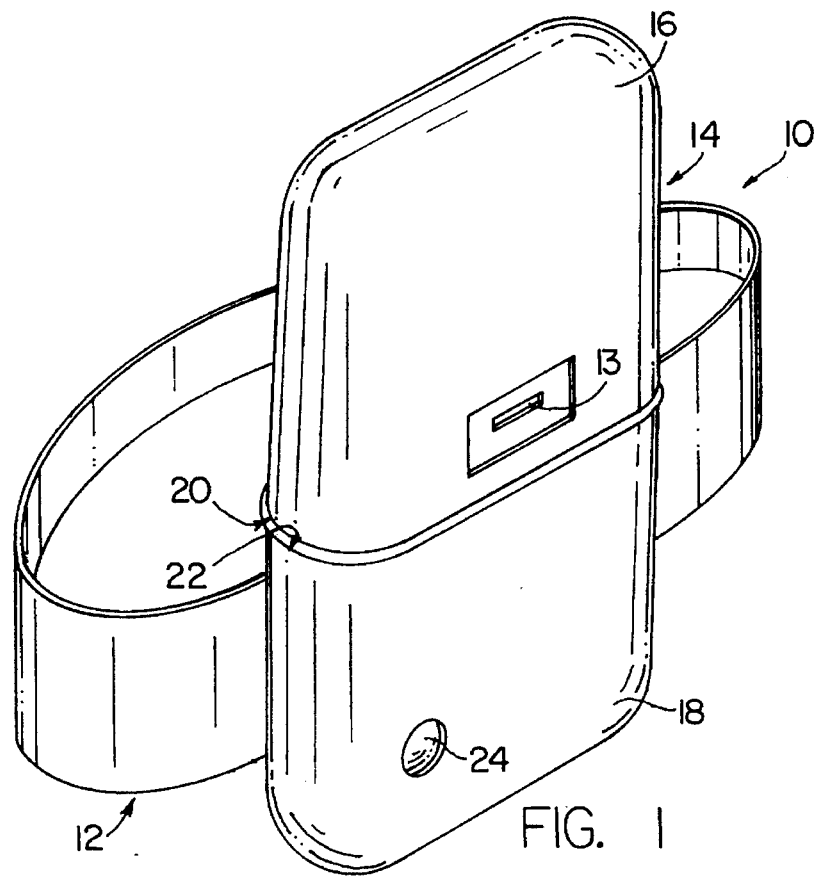
FIG. 1 is a perspective view of the ambulatory pump unit (APU) of the ambulatory medication delivery system embodying the present invention.
Figure 2:
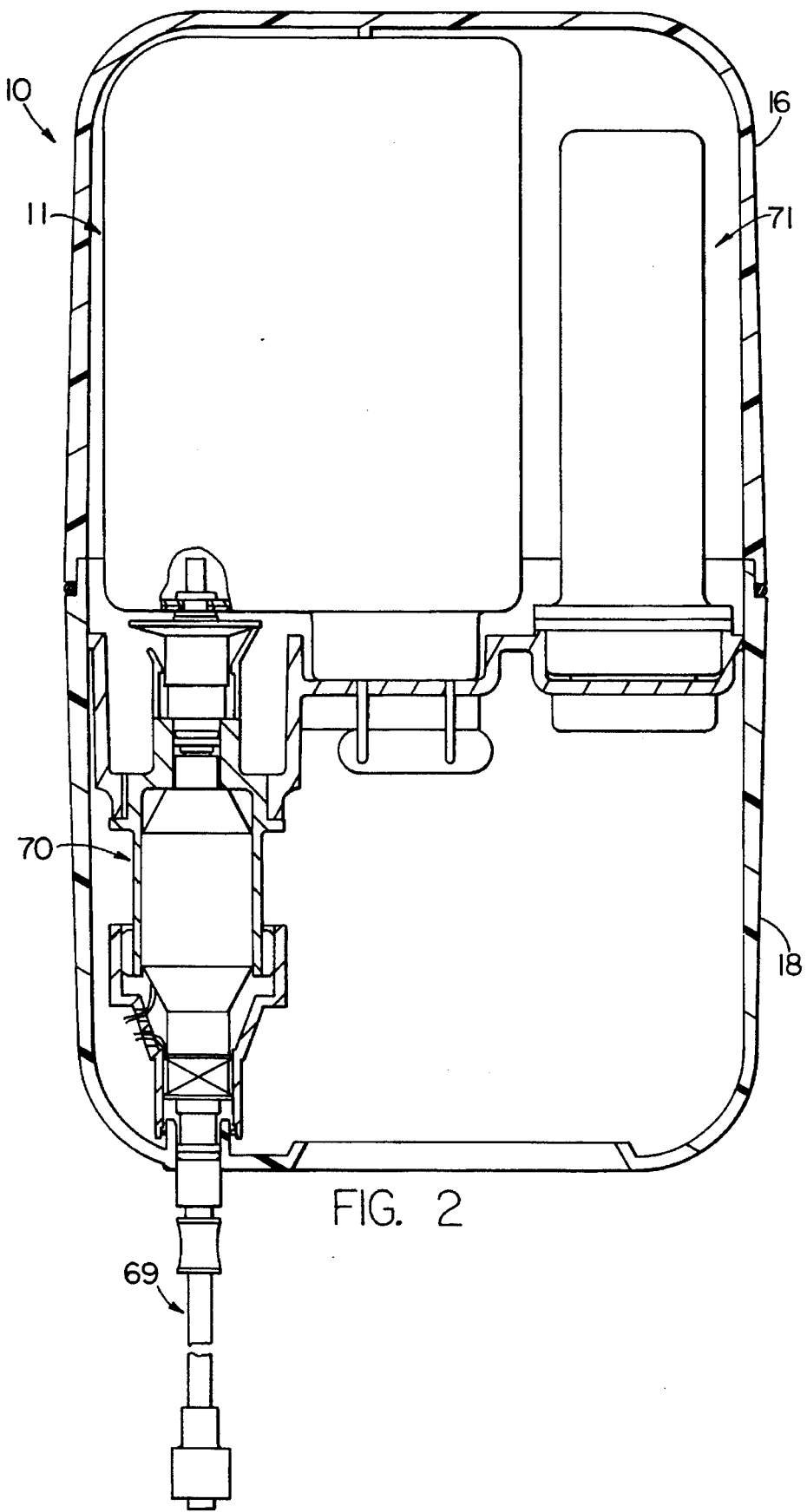
FIG. 2 is a cross-section view of one embodiment of the APU showing the micro-infusion pump (MIP) pumping system used with the ambulatory medication delivery system of the present invention.
Figure 6:
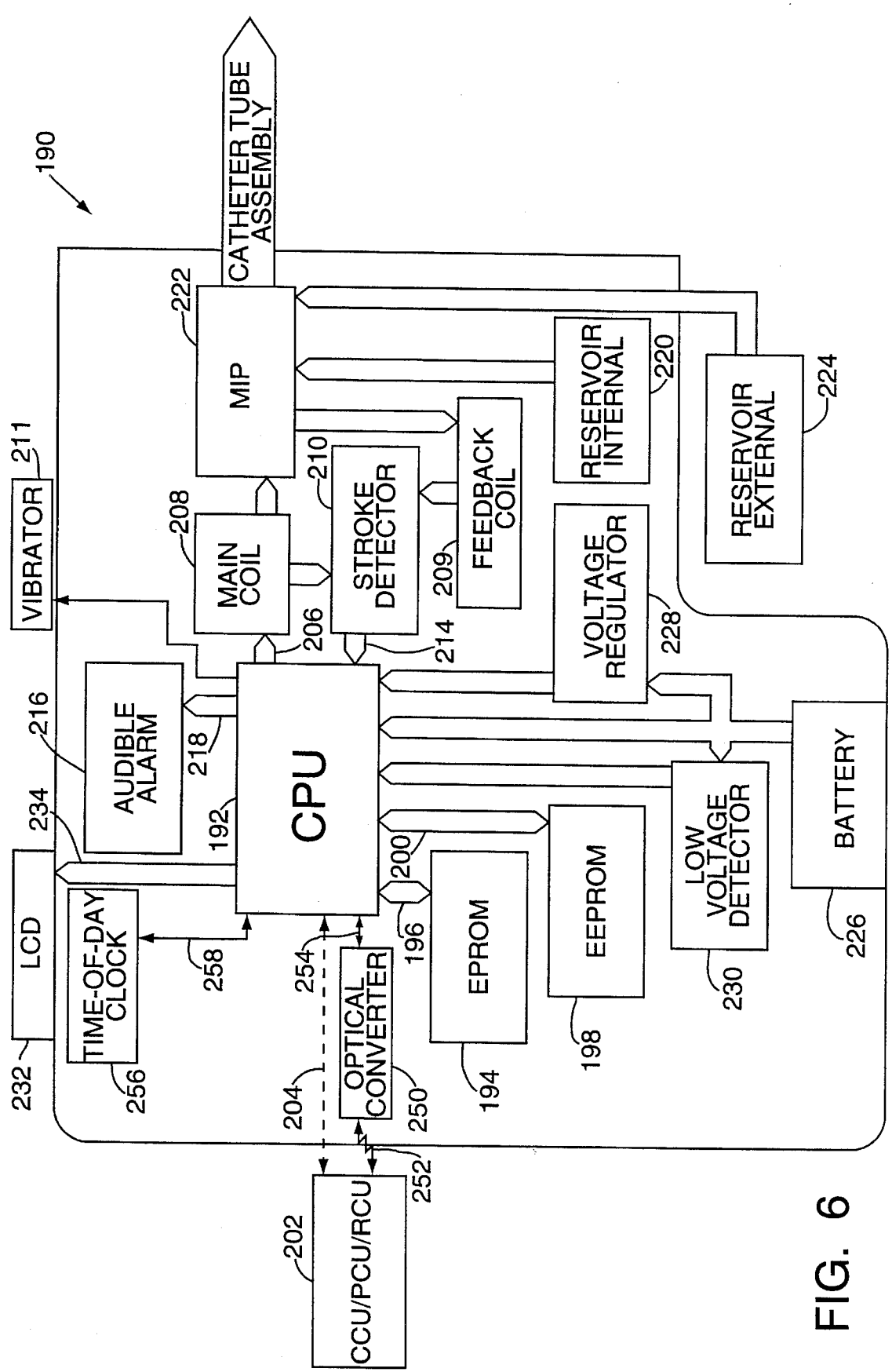
FIG. 6 is a schematic block diagram illustrating the major functional components comprising the APU.
Figure 15:
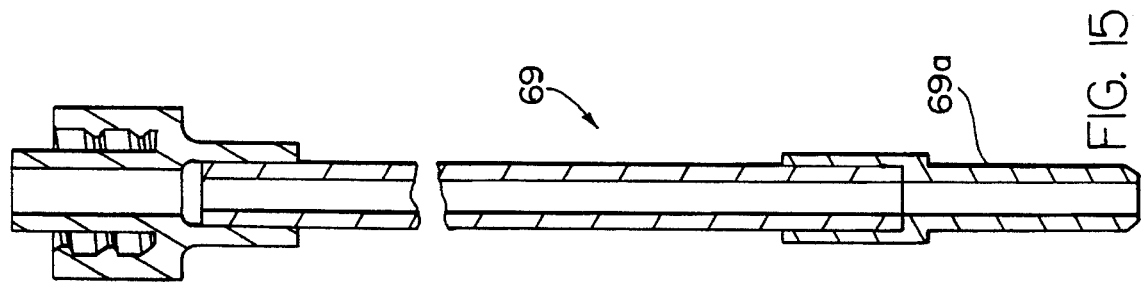
FIG. 15 is a cross-sectional view of the catheter tube line replaceable unit.
Figure 14:
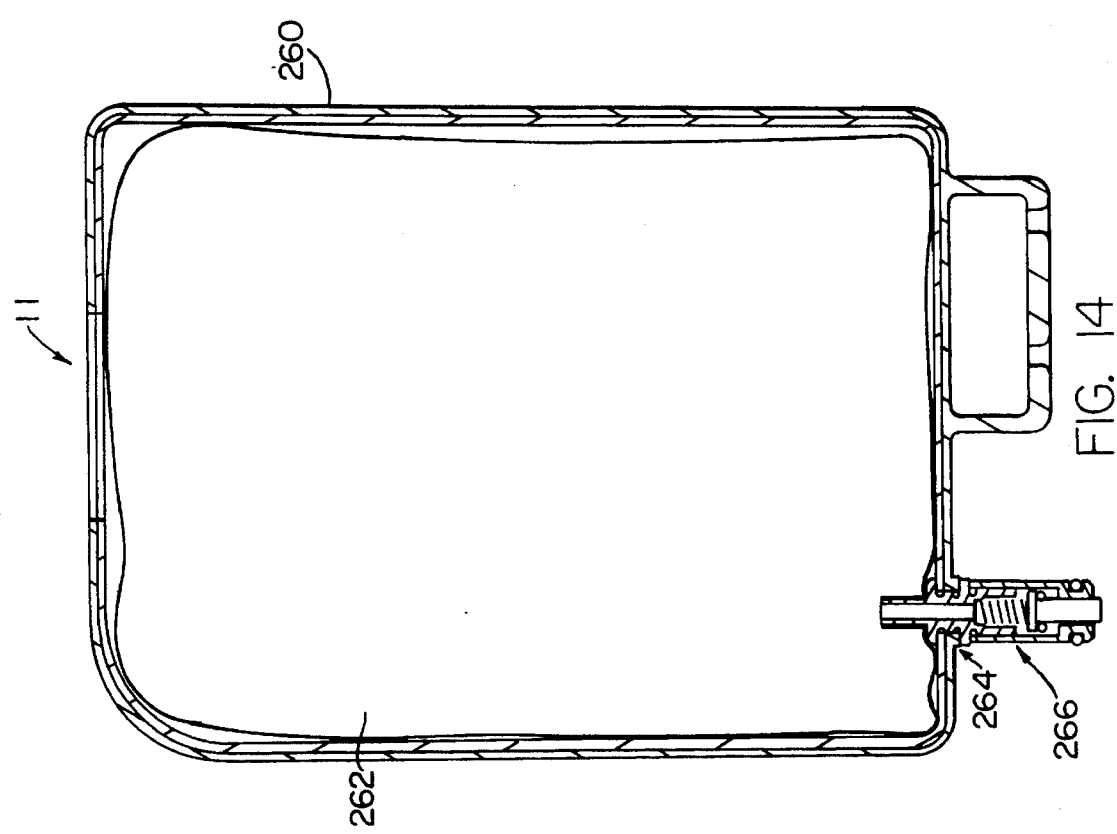
FIG. 14 is an axial cross-sectional view of the fluid reservoir line replaceable unit showing the inlet fitting and shutoff valve.

An ambulatory pump unit referred to herein as the APU and generally designated 10 in FIGS. 1 and 2 and is illustrated as a schematic functional block diagram in FIG. 6 has a case or enclosure 14 which is arranged for easy releasable attachment to a user or patient by means of a strap, Velcro strip or similar arrangement 12 so that the user can move freely about while being infused. The APU 10 is made of a durable, resilient plastic material and has internal chambers for holding among other components, three basic line replaceable units (LRU) which are explained further herein. The term LRU as used in this description defines functionally a component subassembly or part that is easily removed and replaced and preferably is one which is also generally intended to be disposable rather than re-used. The illustrated embodiment of the APU 10 as shown in FIGS. 1 and 2 includes a reservoir LRU (as also shown in FIG. 14) and generally designated 11, a linear motor pump LRU micro infusion pump (MIP) (as also shown in FIGS. 10 and 11) and generally designated 70, and a battery power supply LRU as shown in FIG. 2 and generally designated 71. The APU 10 also includes a digital readout display window 13, internal control and communication electronics, a safety interlock security system, alarm, and a tamper-proof lock assembly. The digital readout display window 13 is located to show through the wall of the APU case 14 as necessary to provide clear visual access. The case or enclosure 14 of the APU 10 is constructed generally in two pieces 16, 18 which are intended to snap together in complementary engagement at their respective open end regions 20, 22 (the open ends are not illustrated in the figures) to form a sealed enclosure 14. An externally accessible and operable button 24 is coupled to the internal control electronics and is recessed within the wall of the APU housing piece 18 to provide user access while preventing inadvertent or accidental contact. The button 24 may be positioned at any convenient location on the APU case 14 and is operated to initiate an "override" condition to cause the APU to deliver medication or fluid in an emergency situation or outside the scheduled delivery time or to provide additional medication in accordance with a predetermined allowance or maximum limit amount preprogrammed and stored within the control memory of the APU 10. The output of the MIP 70 of the APU 10 is coupled to a user by means of a catheter tube assembly LRU generally designated 69 as shown in FIGS. 2 and 15 and a common off-the-shelf and well known catheter LRU (not shown). The APU 10 is described in further detail below.

Clinician Communication Unit

Figure 3:
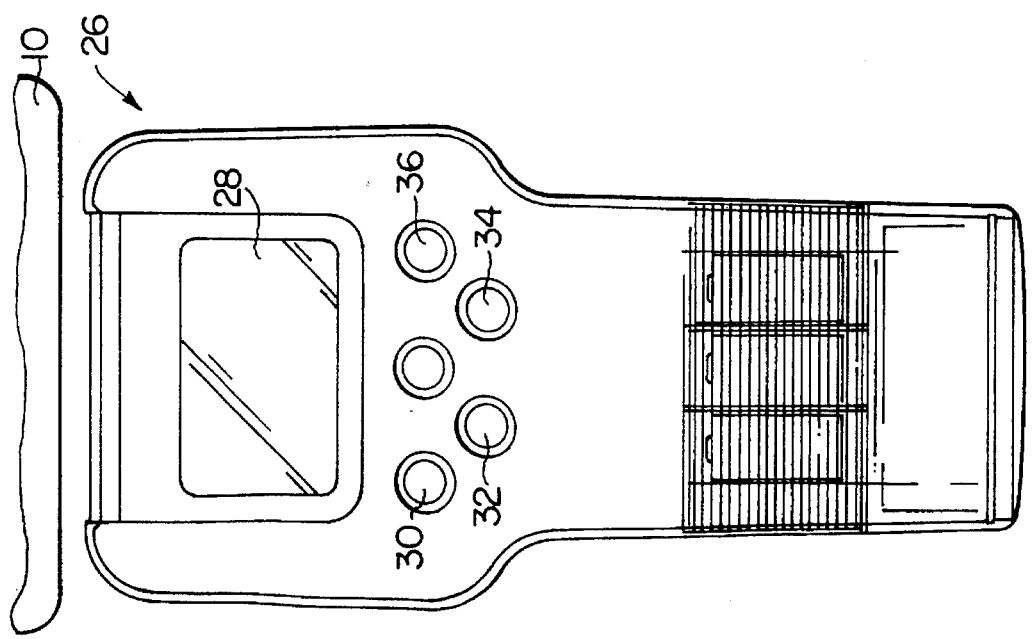
FIG. 3 is a perspective view of the clinician communication unit (CCU) and a partial view of the APU showing the CCU and APU aligned and positioned for communication therebetween.
Figure 7:
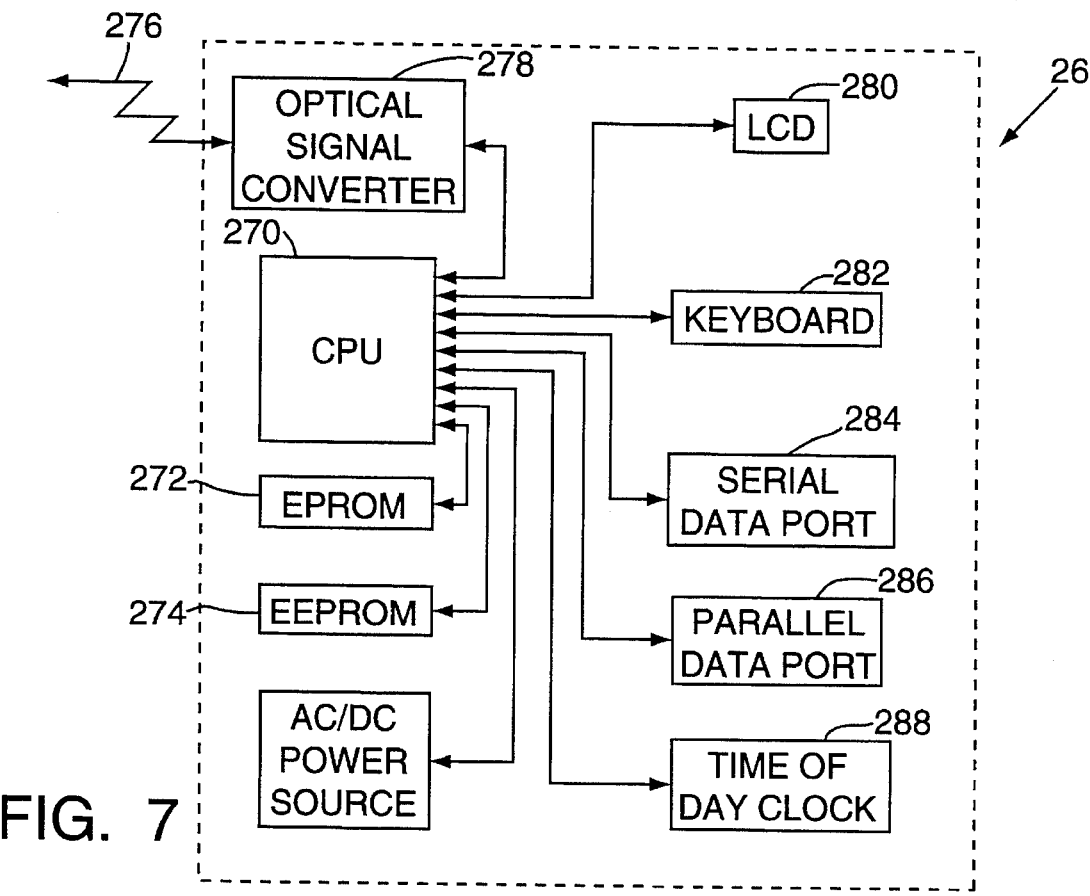
FIG. 7 is a schematic block diagram illustrating the major functional components of the CCU.

The clinician communication unit referred to herein as the CCU is generally designated 26 in FIG. 3 and is illustrated as a schematic functional block diagram in FIG. 7. The CCU 26 is a full-authority, user-friendly, hand-held, unit for use by a clinician or other trained healthcare professional personnel, such as a nurse or pharmacist, and is conveniently portable from one patient location to another. The CCU 26 functions to retrieve information stored in the memory of the APU 10 and to re-store the information in its memory for subsequent downloading to the resident host computer when the healthcare worker is in the process of making rounds or visits to various locations or after completion of his/her rounds of the patient locations. The CCU 26 and APU 10 communicate by means of optical signals, preferably infrared, to retrieve and send information to and from each respective memory.

The CCU 26 includes a display screen or viewing area 28 for displaying instructions or messages received from the host computer, displaying in a form readable by a viewer information retrieved from the memory of the APU 10, displaying in a form readable by a viewer other communications and information that require the attention of or action or response to by the healthcare worker. One typical use of the CCU 26 is to program or enter a set of instructions into the memory of the APU 10 by responding to a menu of commands displayed on the screen 28 and which commands require a response or action thereto. The response or action to the menu of commands is effectuated by operating one or more of the response buttons 30, 32, 34, 36, respectively located on the face of the CCU 26. One such response may be to select from one of a number of options presented on the screen 28 such as increasing or decreasing the time that fluid or medicant is pumped whereby each operation of the response button increments or decrements the displayed time accordingly with the revised information being subsequently or substantially simultaneously communicated to the APU. Menu selection response techniques are known in the art and have been accepted as a simple, error-free, and user-friendly method and means of keyboard communication. The CCU 26 is described in further detail below.

Patient Communication Unit

Figure 4:
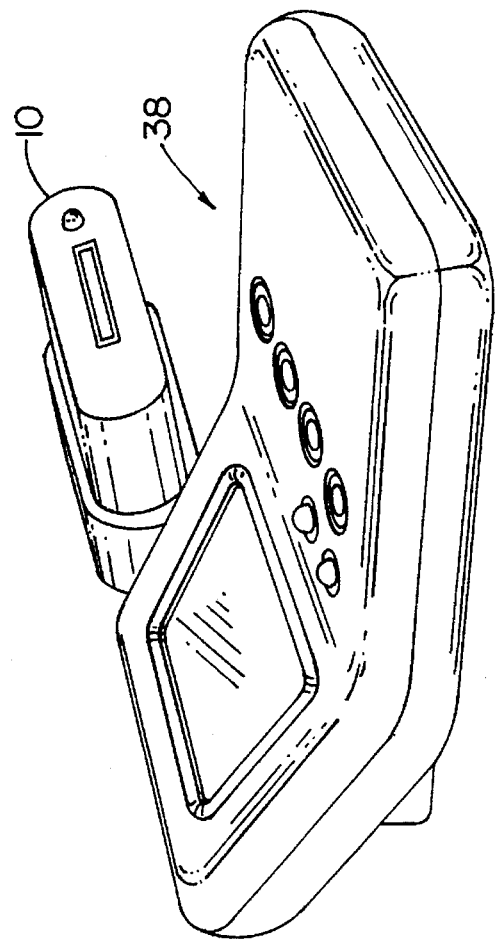
FIG. 4 is a perspective view of the patient communication unit (PCU) and the APU showing the APU and CPU aligned and positioned side-by-side for communication with the APU and a remote host computer base unit via the APU.
Figure 8:
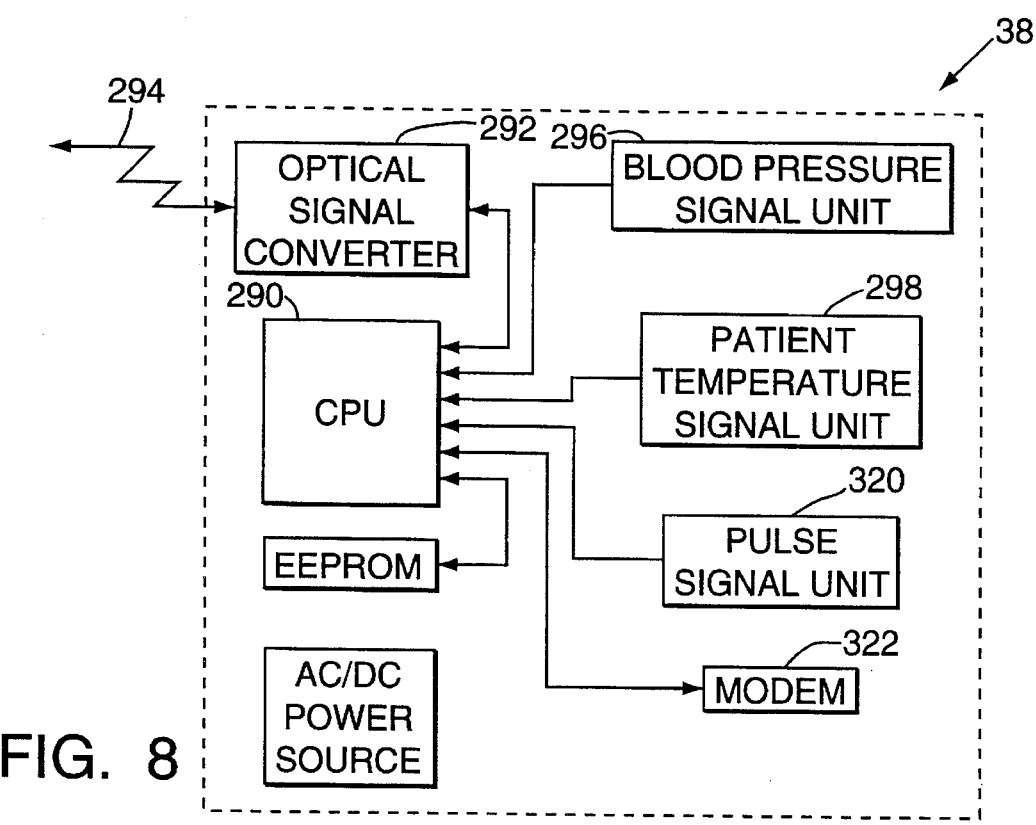
FIG. 8 is a schematic block diagram illustrating the major functional components of the PCU.

The patient communication unit referred to herein as the PCU is generally designated 38 in FIG. 4 and is illustrated as a schematic functional block diagram in FIG. 8. The PCU 38 is not a full-authority unit and is intended for patient use to communicate with a remote host computer. The PCU 38 functions interactively with the patient who responds to prompt signals such as flashing indicator lights or an audible or tactile alarm generated as a result of command generated at and communicated from the remote host computer. The PCU 38 communicates with the APU 10 using optical signals in a similar manner as described above for the CCU 26 and APU 10. The PCU does not store information but rather functions to transfer information to and from the APU to a clinician located remotely from the patient.

Host Computer Base Unit

The host computer base unit includes a computer configured with memory, data storage devices for reading and writing data, internal and external data bus access, printer and communication capabilities and other conventional features such as, CD-ROM, multi-media, and tape backup and storage, and other such capabilities and features well known in the art. The computer operates in accordance with an instruction set and operating system to provide a patient information database, medication profiles, communication control, monitoring control, identification protocols, operation control and other such features and functions as are readily apparent from the description herein. Although one host computer base unit may accommodate theoretically an unlimited number of communication units (APU, CCU, PCU), practical considerations dictate that there may be more than one host computer base unit in a given geographic area, for example, there may be more than one healthcare facility or hospital in an geographic area with each such facility or hospital providing ambulatory healthcare to its patients.

Figure 5:
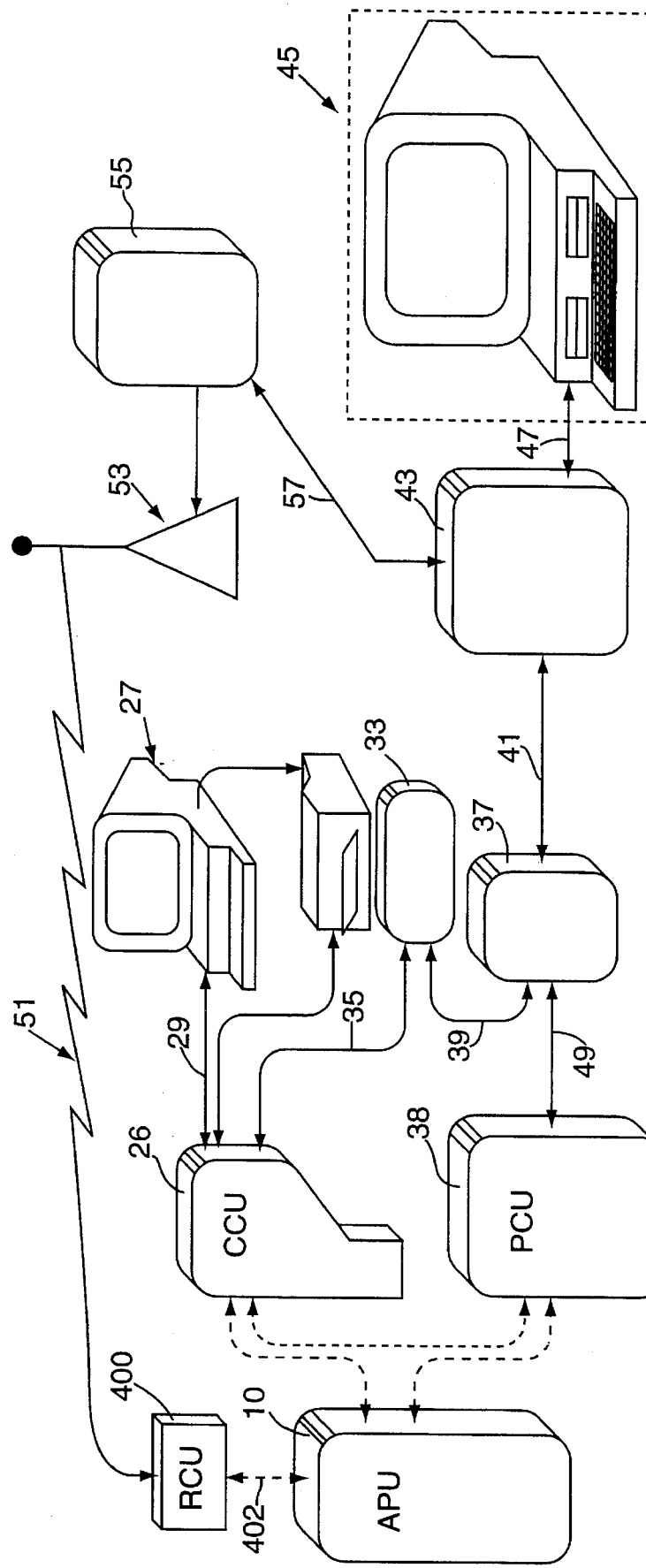
FIG. 5 is a schematic functional block diagram showing the major communication paths to and from the APU (and CCU and PCU) at a patient location and between a patient location and remote location.

FIG. 5 is a schematic functional block diagram and illustrates various communication paths between the main modules or component assemblies of the ambulatory medication delivery system embodying the present invention. As stated above and as illustrated in FIG. 5, information that has been transferred to and stored in a memory medium or device in the CCU 26 may be subsequently retrieved by a resident computer 27 via communication path 29 or by a remote host base computer 45 for downloading, printing, and/or evaluation. The CCU 26 communicates with the remote host base computer 45 by means of a modem 33 coupled to the CCU 26 via the communication path 35. The modem 33 in turn is coupled to a telephone jack 37 via the conductor 39 to establish a dial-up telephone line jack accessed communication link generally designated 41 to a modem 43 at the remote monitoring location. Such telephone line communication links via modems are well known in the art. The modem 43 is coupled to the remote host base computer 45 by the conductor 47 to complete the transfer of the retrieved information from the APU 10 at the patient location to the host base computer at the remote monitoring location. The CCU 26, as a full-authority unit, is utilized to effectuate a number of functions such as, for example, to enter and activate or clear a medication profile program stored in the memory of the APU, prime the pumping system when the medication or fluid supply is initially coupled into the APU, run self-test and diagnostics on the instruction set program and microprocessor of the APU, set alarms, download information to a computer or printer, and perform other functions as is apparent when taken in context in this description.

Turning to FIG. 7, a schematic functional block diagram of the CCU 26 is illustrated therein and includes a CPU represented by the function block 270 which operates in accordance with a set of instruction steps programmed in a memory device such as the EPROM device 272 which is coupled to the CPU. An EEPROM device 274 is used to store the information specifying the medication delivery procedure or fluid administration profile or other operating parameters and communicates with the CPU via an addressing, data and control bus. The delivery procedure or fluid administration profile may be altered as required by the clinician and the data representing a new profile is read into the EEPROM 274 from the CPU 270. The CPU 270 in turn receives data communicated to it from the APU by means of an infrared data link 276 which is used to communication information to and from the APU and CCU. An optical signal converter represented by the function block 278 transforms the optical signals into electrical digitally coded signals which are coupled to the CPU 270. The optical signal converter 278 also receives information from the CPU 270 and converts the digitally encoded signals to optical signals for transmission via the infrared link 276 to the APU. The CCU additionally includes an LCD display represented by function block 280, keyboard represented by the function block 282 for inputting information to the CCU in response to menu prompt as discussed above. The CCU 26 further includes a serial data port represented by function block 284 for communicating and interfacing serial data between a personal computer, modem, printer, or other RS 232 type communication device with the CPU 270. A parallel data port represented by the function block 286 is used to print to a local printer as controlled by the CPU 270. The CCU 26 also includes a time-of-day clock represented by the function block 288 and which is used to provide information to the CPU 270 which in turn provides character generation for display on the LCD 280.

Still considering FIG. 5, information from the APU 10 may also be communicated from a patient location to the remote monitoring location using the PCU 38 which includes an internal modem which in turn is coupled to the telephone jack 37 by the conductor 49 to establish a dial-up telephone line jack accessed communication link and which link is shown generally as 41. The PCU 38 is also used to transmit a patient or user's vital signs, for example, but not limited to pulse rate, blood pressure, temperature, respiration, etc., to the remote host computer base location at which location a clinician can monitor, record and/or respond to variations in or needs of the user as warranted by the informational content of the vital signs.

Turning to FIG. 8, a schematic functional block diagram of the PCU 38 is illustrated therein. The PCU 38 includes a CPU represented by the function block 290 which operates in accordance with a set of instruction steps in a manner similar to that of the CPU of the CCU described above. The PCU also includes an optical signal converter represented by the function block 292 and is used to communicate via an infrared optical link 294 to transmit and receive information from the APU. The optical signal converter 292 of the PCU operates similarly to the optical signal converter 278 of the CCU. Unlike the CCU, the PCU 38 includes a number of units designed to receive a patient's vital signs-and in the example of FIG. 8, a blood pressure signal unit represented by the function block 296, patient temperature signal unit 298 and pulse signal unit represented by the function block 320 receive signals from the patient and which provide the respective monitoring information in a manner well known to those skilled in the art. The patient vital signs received from the respective units are input to the CPU 290 which in turn through the program instruction steps analyzes the information for transmission via the optical signal converter 292 to the APU or alternately through a modem represented by the function block 322 for transmission to a CCU 26 or to the host computer base unit as described above in connection with the discussion of FIG. 5.

Still considering FIG. 5, alternate means of communication between the APU 10 and remote host computer 45 may also be used, such as, for example, beeper-type or pager tone radio frequency transmission to forward information to the remote monitoring location from a patient location when a CCU or PCU is not available. In the present embodiment of the information forwarded as radio frequency (RF) signals requires an RF converter located within the APU or an external or auxiliary unit RF converter to send and receive the radio transmission frequencies and to communicate with the circuitry of the APU 10. A remote communication unit referred to herein as the RCU is generally designated 400 in FIG. 5 and is illustrated as a schematic functional block diagram in FIG. 9 and functions to convert received RF signals to optical signals for communication with the APU 10. As illustrated in FIG. 5, a radio frequency transmission communication path generally designated 51 is established between the APU 10 by means of the RCU 400 at the patient location and an antenna 53 at the remote monitoring location. The antenna 53 is coupled to a beeper-type transmitter 55 which energizes the antenna in a well known manner to transmit as radio frequencies the information received from the remote host computer 45. The remote host computer 45 inputs information via communication path 47 to the modem 43 which modem 43 is in turn coupled to the beeper-type transmitter 55 through the communication path 57 between the beeper and modem. The RCU 400 receives the beeper-type RF signals in which are embedded the informational content as directed and controlled by the remote host computer 45. The RCU 400 converts or demodulates the received RF signals in accordance with well known techniques. It is not critical for purposes of this disclosure to identify the specific RF transmission/decode scheme used since such RF beeper-type transmissions are regulated by the Federal Communication Commission and any system employed must meet and comply with the published regulations for such transmissions. Once the RCU 400 receives and converts the RF signals and extracts the coded information contained therein, the information is transformed to coded electronic digital signals and sent to the APU by means of infrared optical signals to establish an infrared optical link 402 between the RCU 400 and APU 10. The APU 10 in turn receives the infrared optical signals and transforms them to coded electronic digital signals for use by the APU.

Turning to FIG. 9, a schematic functional block diagram of the RCU 400 is illustrated therein and includes an RF signal unit represented by the function block 404 receives radio frequency signals shown generally as 406 and converts the radio frequency signals to electrical digitally encoded signals which are input to an optical signal converter represented by the function block 408. The optical signal converter 408 operates similarly as the optical signal converter 278 of the CCU and converts electrical signals to establish an infrared data link 410 to communicate information to and receive information from the APU.

Standard communication protocols are used to establish and maintain the communication link between the remote location and the patient location and error detection and prevention techniques described below insure that the medication or fluid delivery profile is accurately and correctly received at the patient location.

The APU 10 is programmed with an instruction set which contains digitally coded control information that enables the APU to deliver medication using medically approved procedures. This digitally coded information is transferred to the APU 10 from (for example) the CCU 26 using an infrared optical bi-directional data link. The CCU 26 transfers the digital data defining a new medication delivery procedure to the APU 10 and then commands the APU to validate the data by sending the data back to the CCU 26 where the data is checked and compared to the original data transferred. This error checking scheme requires an exact match of data sent to data returned for verification that the data sent to the patient location is error free.

The APU 10 can also receive new medication delivery procedures via a unidirectional radio link. Since the radio transmission data link is unidirectional only it is not possible for the APU to confirm that the data defining the new medication delivery procedure has been properly received and understood. Therefore different error detecting techniques and schemes will be used whenever a unidirectional transfer of new medication delivery procedures occurs.

The first technique for error prevention is to include error detection information along with the data such as a Cyclic Redundancy Check (CRC). By choosing the proper CRC for the amount of data transmitted in a message, the type of error detection that the system will exhibit can be assured. For a given length of message and a type of CRC it can be assured that all single bit errors, double bit errors, . . . etc . . . will be detected. Additionally, redundancy in the data sent provides a high first level of error detection. The CRC error detection scheme is well known to those skilled in the art.

The next technique that is used for error prevention is that parameters in a given medication delivery procedure will have a range of permitted settings. For example, the prescription for a particular medication may range from 10 to 15 milligrams per hour. The EEPROM in the CCU is programmed with a medication delivery procedure which is set at an initial 10 milligrams per hour delivery. The EEPROM is also programmed with the fact that the medication delivery procedure can be increased to 15 milligrams per hour. Any commands transmitted via the unidirectional radio transmission data link to change the medication delivery rate are limited to increase the delivery rate up to the 15 milligrams per hour limit programmed in the EEPROM.

Another technique that is utilized for error prevention is to store multiple sets of medication delivery procedures in the EEPROM in the CCU allowing only one of the possible available sets to be operative at a time. Any information via the radio transmission data link can only command the CCU to begin operation from a different medication delivery procedure selected from the number of sets of medication delivery procedures stored in the EEPROM in the CCU.

A final but not exhaustive error prevention technique available is to send a new medication delivery procedure a multiple number of times with each required to be received and decoded and compared and allowing the change to take place only if all decoded procedures match.

Turning to FIGS. 10 and 11, one embodiment of the micro infusion pump or MIP which may be advantageously used with the ambulatory medication delivery system embodying the present invention is illustrated therein in cross-sectional view and is generally designated 70. The MIP 70 is cylindrically shaped and comprises an axially elongated main body portion or sleeve generally designated 72, an inlet portion generally designated 74 and which inlet portion is coupled to and received by the inlet end 76 of the body portion 72, and an outlet portion generally designated 78 and which outlet portion is coupled to and received by the outlet end 80 of the main body portion 72. The main body portion 72, inlet portion 74 and outlet portion 78 are axially aligned and when assembled form an integral unit. The main body portion 72 has a bore 82 extending axially therethrough and which bore slidingly carries an axially elongated piston assembly generally designated 84. The piston assembly 84 includes an axially elongated piston 86 which is preferably made of a martensitic stainless steel or other suitable material known to those skilled in the art. The outer peripheral diameter dimension D1 of the piston 86 is slightly smaller than the inner diameter dimension D2 of the central bore 82 of the main body portion 72 to permit sliding movement of the piston 86 within the bore 82 but yet provide closely held tolerances to maintain a sealing fit between the outer wall surface of the piston 86 and the inner surface of the bore 82 so as to limit or substantially eliminate any possible fluid leakage between the contacting surfaces of the piston and the bore. The inlet portion 74, outlet portion 78 and piston 86 have an axial bore 88, 90, and 92, respectively extending axially therethrough to provide communication from the inlet 94 of the pump to the outlet 96 of the pump.

The end 98 of the piston 86 nearest the outlet portion 78 carries a "drop-tight" shutoff valve 100 and has an axially facing radial surface 102 which is in sealing engagement with an axially facing surface 108 of an "O-ring" 104 located in position between the outlet portion 78 and the main body portion 72, the respective surfaces 102 and 108 being in facing relationship with one another. The opening of the "O-ring" 104 is coaxial with a cheek portion 106 of the outlet portion 78 and bore 90. The axially facing radial surface 102 of the "drop-tight" shutoff valve 100 has a diameter slightly larger than the inner diameter opening of the "O-ring" 104 to completely occlude the opening in the "O-ring" when the axial facing radial surface 102 is in contact with the axially facing surface 108 of the "O-ring" 104. The "drop tight" shutoff valve 100 is cup shaped and has an axially facing outwardly open end 110 disposed opposite its closed end 112. The cylindrical wall 114 of the shutoff valve 100 has a number of radially extending orifices 116, 118, 120 therethrough to provide communication from the interior of the shutoff valve 100 to the bore 82 within the main body 72 in the region of the shutoff valve.

The bore 88 of the inlet portion 74 axially carries a spring 122 which has one end 124 nested in a spring seat 126 axially carried within the inlet end 128 of the piston 86. The opposite end 130 of the spring 122 is fixedly held within the inlet portion 74 by means of an inlet coupling generally designated 132 which in the embodiment shown has one end 134 in complementary gripping engagement within axial recess 138 in the end 140 of the inlet portion 74. The spring 122 provides a biasing force against the piston assembly 84 to urge the piston assembly 84 in the direction indicated by arrow 142 toward the outlet portion 78 to cause the axially facing radial surface 102 of the shutoff valve 100 to come into pressing contact with the surface 108 of the "O-ring" 104 to provide a leak-proof seal. The longitudinal dimension of the piston assembly 84 is less than the longitudinal distance between the "O-ring" 104 and the innermost axially facing surface 144 of the inlet portion 74 so that a radial gap or space generally designated 146 is defined between the end surface 148 of the piston assembly 84 and the innermost surface 144 of the inlet portion 74 when the piston assembly is in its "drop-tight" or at-rest position. The dimension of the frusto-conical shaped gap 146 is the travel distance of the piston assembly 84 when the piston assembly is moved toward and into contact with the surface 144 of the inlet portion 74 as explained below.

The material of the inlet portion 74 is a metallic material such as martensitic stainless steel or other suitable material which may be machined as required to achieve the necessary dimensions and tolerances. Typically, the inlet coupling 132 is bonded to the inlet portion 74 by means of a suitable bonding material approved for use by the Food and Drug Administration (FDA).

In the illustrated embodiment a duckbill type check valve 150 is held between the piston 86 and the "drop-tight" shutoff valve 100 to allow fluid flow in a direction from the inlet 94 to the outlet 96 and to prevent fluid flow in the direction from outlet 96 to inlet 94. Typically such check valves are made of an approved elastomeric material well known in the medical field and the valve operation understood by those skilled in the art.

A second duckbill type check valve 152 is held near the innermost end of an axial recess region 153 in the outlet end 154 of the outlet portion 78 by means of an inner end portion 155 of an outlet coupling 157 which is inserted into and held in complementary gripping engagement within the axial recess 153 to permit flow in a direction from the inlet 94 to the outlet 96. Typically, the outlet coupling 157 is bonded to the outlet portion 78 by means of a suitable bonding material approved for use by the Food and Drug Administration (FDA).

In operation, the MIP 70 has the open or inlet end 156 of the inlet coupling 132 attached to a source of fluid, medication and the like. The pump is "primed" to fill the axial bore 88 within the inlet portion 74, the bore 92 within the piston 86 and the bore 90 within the outlet portion 78. Pump filling action occurs when the piston assembly 84 is moved by magnetic force (as explained below) toward the inlet end 94. An incremental volume of fluid is drawn through the check valve 150 because it opens when moved in the direction of arrow 141, due to pressure exerted against the valve as it moves with the piston, flows through the orifices 116, 118, 120 of the shutoff valve 100 and into a chamber 113 within the main body 72 in the region of the shutoff valve. The chamber 113 has a volume substantially defined by the piston diameter D1 and piston stroke. Simultaneously, an incremental volume of fluid is extruded from the piston frusto-conical shaped chamber gap 146. When the piston assembly 84 is returned to its at-rest position by action of the spring 122, the pumping volume chamber 113 is reduced thereby forcing the incremental volume of fluid that was added to the chamber 113 when the piston moved to close the chamber gap 146, through the check valve 152 and out of the pump. Simultaneously, an incremental volume of fluid is drawn into the piston frusto-conical shaped chamber gap 146. The check valve 150 carried by the piston assembly 84 is forced closed when the piston assembly moves in the direction of arrow 142 toward the outlet due to the pressure exerted against the valve as it moves with the piston to push or expel the fluid from the outlet.

The characteristics of the spring. 122 are chosen so as to provide a desired pumping pressure when the spring 122 forces the piston assembly 84 to move toward the outlet to expel a desired incremental volume of fluid. The spring 122 is preset at the time of manufacture to provide a given predetermined force at a given stroke length. Since the spring force is held to a very close tolerance, there is substantially no variation in pressure from one unit to another. Further, pumping accuracy is maintained because the pumping pressure does not vary from pump cycle to pump cycle as is common in peristaltic and other type pumps.

Figure 12:
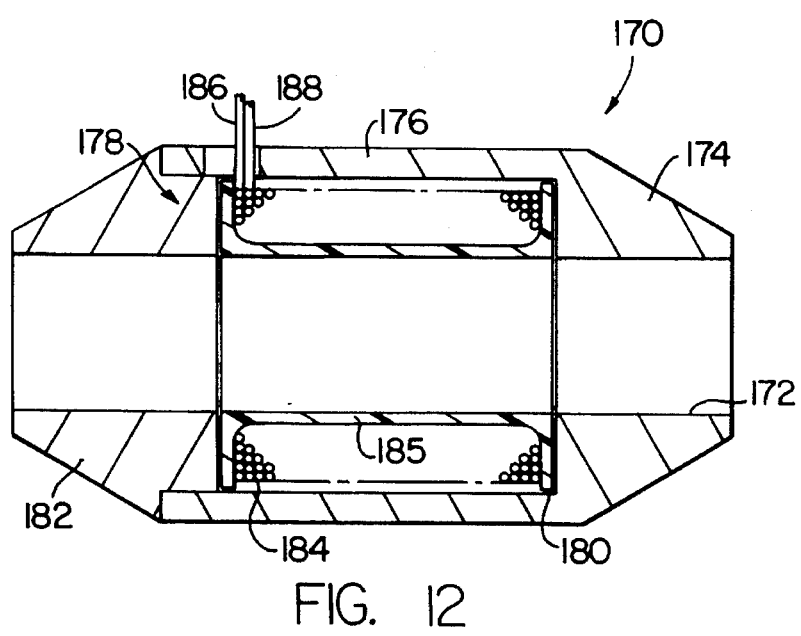
FIG. 12 is an axial cross-sectional view of the electromagnet encasement unit used with the MIP of FIG. 2.

A bobbin assembly and coil unit or electromagnet encasement unit generally designated 170 is shown partially in FIGS. 10 and 11 and is illustrated in greater detail in an axial cross-sectional view in FIG. 12. The electromagnet encasement unit 170 has an axially elongated central bore 172 which is dimensioned to slide and fit coaxially over the outer peripheral surface of the cylindrically shaped main body portion 72. The electromagnet encasement unit 170 is made up of a cup shaped form piece 174 which has an outer cylindrical wall 176 to define a cavity to receive a bobbin 180 and an end cap 182 which fits into the open end 178 of the cavity to hold the bobbin 180 therein. The bobbin 180 is generally made of an nonferrous material and has a cylindrical wall 185 which serves as a winding form. A wire coil 184 is wound on the bobbin 180 to form an electromagnet and a magnetic field is generated when a suitable voltage potential is applied across the respective ends 186, 188 of the coil 184.

In operation, magnetic flux passes from the electromagnet encasement unit 170 through the wall 73 of the main body portion 72, into the piston 86, across the frusto-conical shaped gap 146 to the inlet portion 74, and returns to the electromagnet encasement unit to complete the magnetic path. The magnetic flux across the gap 146 tends to pull or attract the piston 86 toward the inlet portion 74 and when a sufficiently strong magnetic field is developed to overcome the biasing force of the spring 122, the piston 86 moves to close the frusto-conical shaped gap 146 and compress the spring. The spring 122 will remain in compression until such time that the magnetic field is removed or reduced to an intensity insufficient to overcome the spring force. When the magnetic field is removed, the force of the expanding spring 122 will cause the piston 86 to move in a direction indicated by arrow 142 toward the outlet 96. The check valve 150 carried by the "drop-tight" shutoff valve 100 is closed when the piston moves in the direction toward the outlet 96. The volume of the outlet chamber is thus reduced by an amount equivalent to the distance and area traveled by the piston 86 and an equivalent volume of fluid is discharged from the outlet 96 through the outlet check valve 152.

Since the piston 86 and spring 122 are carried within the main body portion 72, inlet portion 74 and outlet portion 78 as explained above, and the piston 86 and spring 122 are only magnetically coupled through the wall 73 of the main body portion 72, the piston assembly, spring, main body portion and inlet and outlet portions are considered to be a LRU and therefore discardable and replaceable with another unit. The ability to easily remove and replace the moving parts of the MIP insures that a sterile assembly can be used, facilitates repair and permits the use of a low cost pumping element.

A further unique feature of the LRU of the MIP 70 as also explained above, is the ability to specifically control the incremental volume of fluid pumped by controlling the length of the stroke of the piston 86, i.e. increasing the gap 146 increases the volume of fluid pumped each stroke and decreasing the gap 146 decreases the volume of fluid pumped each stroke. A number of different pumping volume LRU's of the MIP 70 can be manufactured to accommodate a range of desired pumping volumes with each desired pumping volume only requiring the proper LRU to be used with the MIP 70. No external adjustments or "fine tuning" is required to obtain a desired incremental pumping volume.

The timing of the pumping action of the MIP 70 is controlled by a microprocessor and associated electronic circuitry which operates in accordance with an operating instruction set stored within a memory therein. Voltage signals, as explained in further detail in connection with the discussion of FIG. 13, are generated at the closing of a respective air gap present at each end of the piston assembly 84 when the piston moves completely in one direction by the magnetic force developed or in the opposite direction by the spring force. A voltage signal having a spike shaped characteristic is developed due to the air gap being closed and the presence of the voltage spikes is used as feedback signal which is detected by the microprocessor to assure the piston 86 has been fully drawn to close the chamber 146. A second wire coil 300 which functions as a feedback coil is wound on a bobbin 302 having a cylindrical wall 304 which serves as a winding form. The bobbin has an axially elongated central bore 306 which is dimensioned to slide and fit coaxially over the outer peripheral surface of the cylindrically shaped main body portion 72 at the outlet end 80. The second wire coil is energized weakly by applying a voltage to the leads 308, 310 so that a voltage spike is generated when the shutoff valve 100 closes the gap created when the piston moves toward the inlet end. The voltage spike generated when the piston moves to its at rest position is detected by the microprocessor to assure the piston 86 has fully moved to its at rest position to complete the pumping cycle. The feedback coil is energized at the time the electromagnet coil 184 is energized and remains energized for a predetermined time after the coil 184 is de-energized in order to sense the presence of the voltage spike produced due to the closing of the gap at the end of the pumping cycle. If the two voltage spikes are not detected by the microprocessor within a predetermined time interval, the microprocessor concludes there is a failure of some type, line blockage at either the input or output or due to some other reason and as explained below activates an alarm.

Turning to FIG. 6, a schematic functional block diagram of an illustrative ambulatory pump unit (APU) is illustrated therein and is generally designated 190. A central processing unit (CPU) or microprocessor 192 operates in accordance with a set of instruction steps programmed in an external memory device such as the electrically programmable read-only-memory (EPROM) device 194. The operation of the CPU 192 is generally well understood by those skilled in the art and reference can be made to textbooks and technical literature for additional information if such information is needed. For purposes of this disclosure, it is sufficient to state that the CPU operates in a normal manner and requires a memory device to hold the program or operating instruction set. The steps of the program instruction set are sent to the CPU 192 from the EPROM 194 via the addressing, data and control bus 196. An EEPROM (erasable electrically programmable read only memory) device 198 is used to store the information specifying the medication delivery procedure or fluid administration profile or other operating parameters and communicates with the CPU 192 via the addressing, data and control bus 200. The terms medication delivery procedure or fluid administration profile are understood in the art and define the times and amount of fluid to be delivered by the ambulatory fluid delivery system to a given patient. The delivery procedure or fluid administration profile may be altered as required by the clinician and the data representing the new profile is read into the EEPROM 198 from the CPU 192. The CPU 192 in turn receives the data from the host computer via the CCU 26 or PCU 38 collectively represented as function block 202. The CCU 26 or PCU 38 in function block 202 in turn may be coupled to the CPU 192 via hard wiring or a bus 204 shown in phantom. Preferably, the CCU or PCU is optically coupled to the CPU by means of an infrared optical link. The APU 190 includes an optical receiver and converter and is represented by the function block 250. Optical signals generated at the CCU or PCU are carried by the infrared optical link 252 and are converted to digitally encoded data signals which are input to the CPU 192 via the bus 254. In any event, the necessary addressing, data and control signals are coupled to the CPU from the CCU or PCU.

As described above in connection with FIG. 5, the CPU 192 can also receive RF (radio frequency) signals when a CCU or a PCU is not available. The RF signal is received by the RCU 400 where the RF signal is transformed and processed for transmission. Typical type actions communicated via the CCU or PCU or by RF and which may require some action include changing fluid administration profiles, priming the MIP, battery replacement alarm response and so forth.

The CPU 192 provides a control signal via the bus 206 which is used to cause the connection of a voltage potential to the piston driving electromagnet coil represented by function block 208. The control signal is generated in accordance with the program instruction set stored in the EEPROM 198 and the applied voltage potential causes the electromagnet coil 208 to become energized at the predetermined time as specified in the program instruction set. A stroke detector functions to insure a complete pumping cycle occurs and is represented by function block 210. The stroke detector function may be included in the program instruction set in the CPU wherein voltage spikes generated in the electromagnet coil 208 and a secondary coil represented by function block 209 as the piston moves to close the gap at either end of its stroke are used to sense the completion of a pumping stroke. The stroke detector 210 sends a signal to the CPU 192 via the lead 214 to indicate that the pump piston has completed its stroke within a predetermined time interval band. The time duration of the piston pump stroke is known from the design of the pump and the viscosity of the fluid and is verified by test. The allowable stroke time band or cycle interval is entered as data into the EEPROM 198 or alternately may be a self-calibrating process. The CPU 192 monitors the respective pump stroke times from the stroke detector 210 and compares the monitored time with the predetermined allowable time band.

If the pump stroke time is not within the allowable time band, an alarm signal is generated by the CPU 192 and sent via lead 218 to the alarm circuit represented by function block 216. Typical conditions which may cause such an alarm to be generated include no fluid being drawn from the internal reservoir represented by function block 220 coupled to the pump 222, occlusion, or excess air in the fluid pumping passageways of the pump connections or tubing. The APU 190 also accommodates coupling an external reservoir represented by the function block 224 to the pump 222 when the reservoir is too large to be contained within the APU.

The APU 190 is powered by a battery pack as represented by function block 226. The battery pack 226 is coupled to a voltage regulator circuit shown as function block 228 which in turn provides a regulated voltage to the CPU 192. A low voltage detection circuit 230 is also coupled to the battery pack 226 and to the CPU 192 and which functions to generate a signal which is sent to the CPU when the battery pack voltage drops below a predetermined threshold. The CPU 192 in turn recognizes a low voltage warning condition and sends an alarm signal to the audible alarm circuit 216 via a lead 218, and may also be sent to a vibrator or other tactile device represented by function block 211. The vibrations from the vibrator are used to alert the user that the battery pack 226 requires recharging or replacement with a freshly charged battery pack.

The APU 190 also includes a liquid crystal display (LCD) screen 232 coupled to the CPU 192 via the bus 234 and which LCD screen is used to visually display messages, warnings, diagnostics, and other information in readable form to the user. The CPU generates the characters displayed on the LCD screen in accordance with display generation techniques well understood by those skilled in the art. Although an LCD screen 232 is disclosed, it is understood that any suitable display means and technology may be used with the APU.

The APU 190 also includes a time-of-day clock represented by the function block 256. The clock signals are coupled to the CPU 192 via lead 258 and are converted by the CPU in accordance with display generation techniques to provide the appropriate numerical characters on the LCD screen to show the time-of-day.

Turning now to FIG. 13, a graphic representation of several characteristic voltage curves are illustrated showing the magnitude of the voltage potential of a battery versus time wherein time represents the battery life. The voltage characteristics curve 236 represents the battery supply voltage potential characteristic over the battery lifetime. The battery voltage potential is applied to the electromagnet coil 208 to generate a magnetic field to move the pump piston and to the secondary or feedback coil 209 as explained above. The characteristic curve 236 illustrates a series of short duration almost spike-like dips 238, 238 in the voltage potential and appear each time the piston closes the gap during the pumping cycle at each end of the stroke. This characteristic and well defined change in the voltage and current is sensed and used by the CPU 192 for timing control. As explained above, the time duration of a piston stroke is known and therefore the CPU can measure the time interval between the voltage spike signals generated by the main coil and the secondary or feedback coil. If the voltage signals do not occur within a predefined time window, the CPU recognizes that a failure of some type has occurred and takes the appropriate action in accordance with the program instruction set.

Although the characteristic curve 236 is representative of the battery supply voltage potential, the operation of the electronic circuitry is at a lower regulated voltage having a representative magnitude indicated by the voltage characteristic curve 240. The voltage characteristic curve 242 represents the voltage potential threshold magnitude below which a first low voltage warning signal is generated when the magnitude of the voltage potential of the battery falls below the threshold level. It is seen that the first voltage threshold level represented by the characteristic curve 242 is substantially above the magnitude of the regulated voltage potential represented by the voltage characteristic curve 240 and therefore, some appreciable time may elapse before the magnitude of the battery supply voltage potential drops dangerously low to the level of the regulated voltage magnitude. The time interval over which the magnitude of the battery supply voltage potential deteriorates from the first voltage threshold level magnitude to the regulated voltage magnitude is illustrated as $t_1$. The voltage characteristic curve 244 represents the voltage potential threshold magnitude below which a second low voltage warning signal is generated when the magnitude of the battery voltage potential falls below the threshold level. Again, it can be seen that the regulated voltage potential magnitude represented by the characteristic curve 240 is still substantially below the second low voltage warning threshold level and still provides a time interval illustrated as $t_2$ in FIG. 13 before the battery voltage potential magnitude drops to the level of the regulated voltage potential magnitude. The second low voltage warning still provides time to replace the discharged battery with a freshly charged battery. The first and second low voltage warning still provides time to replace the discharged battery with a freshly charged battery. The first and second low voltage warning signals can be distinct from one another and may be audible, visual, vibratory or combinations thereof. As is well understood in the art, the time interval over which a battery drops from a fully charged voltage potential to a less than fully charged voltage potential is dependent upon the battery itself, the electrical application with which the battery is used and so forth. For example, it is reasonable to expect that a battery will reach a discharged state in a shorter interval of time if the pump is continuously operated in comparison to intermittent operation.

FIG. 14 is an axial cross-sectional view of one embodiment of a fluid reservoir that may be used with the APU of the present invention. In FIG. 14, the reservoir 11 includes a case 260, a flexible bag 262 carried within the case 260 and conforming generally to the internal shape of case. The case 260 also includes an engaging and holding profiled opening 264 for receiving a connecting assembly 266 which is bonded to the bag 262 using FDA approved bonding or adhesive materials and methods. The connecting assembly 266 is inserted into the inlet coupling of the MIP for fluid flow as illustrated for example in FIGS. 2, 10 and 11. Alternately, the case 260, bag 262 holding the medication or fluid and connecting assembly 266 may be a single integral unit with the prescription identification being made part of the APU case or applied to the case 260 and viewed through the APU case wall.

FIG. 15 illustrates an axial cross-sectional view of a typical catheter tube assembly 69 for connecting the outlet of the MIP to an infusion needle assembly. The cather tube assembly 69 has an end 69a which is dimensioned and configured to be complementarily received with the outlet connecting coupler 157 at the outlet end 96 of the MIP. The remaining portions of the catheter tube and infusion needle assembly are commonly known.

An ambulatory medication delivery system including a portable infusion unit having a computer controllable microinfusion pump embodying the present invention has been described above in several preferred embodiments. It will be recognized that numerous changes and modification may be made by those skilled in the art without departing from the spirit or scope of the invention and therefore the invention has been described by way of illustration rather than limitation.

I claim:

1. An ambulatory medication delivery system for delivering at least one fluid to a patient, comprising:
   portable infusion means comprising, in combination:
   at least one reservoir means for storing a supply of fluid to be delivered to the patient;
   tube communication means for delivering said fluid to the patient
   at least one controllable pump means having a fluid inlet for receiving said fluid from said at least one reservoir means and a fluid outlet for discharging said fluid received at said pump inlet, said controllable pump means including;
   an axially elongated main housing having an inlet end portion connected with the fluid inlet, an outlet end portion connected with the fluid outlet and a cylinder bore extending therethrough between said inlet and said outlet end portions;
   piston means slidably mounted within said main housing cylinder bore for reciprocating motion along on axial path having end points respectively in the inlet and outlet end portions, the piston means and the cylinder bore defining a variable volume pumping chamber between the piston means and the outlet end portion of the housing and communicating with the fluid outlet;
   spring means connected with the piston means for moving said piston means along the axial path toward said outlet end portion of the housing in a pumping stroke;
   drive means for moving said piston means along the axial path toward the inlet end portion of the housing in an intake stroke and in opposition to the spring means;

each intake stroke and pumping stroke of the piston means between the end points of the axial path causing a predetermined incremental volume of fluid to be pumped from the variable volume pumping chamber into the fluid outlet;

shutoff valve means defined at the outlet end portion of the housing and actuated by the motion of the piston means along the axial path in the cylinder bore at the outlet end portion of the housing for cutting off fluid communication between the variable volume pumping chamber and the fluid outlet when the piston means reaches the end point in the outlet end portion of the housing;

whereby fluid in said variable volume pumping chamber is expelled from said fluid outlet when said piston is moved along the axial path in a direction from said inlet end portion to said outlet end portion and fluid is prevented by the shutoff valve means from flowing from said fluid outlet when said piston means is at rest at the end point of the path in the outlet end portion of the housing;

means for coupling said pump fluid inlet to said at least one reservoir means;

means for coupling said pump fluid outlet to said tube communication means;

control means coupled to said at least one controllable pump means for activating said pump means to pump said predetermined incremental volume of fluid from said reservoir in response to a pump control signal generated by said control means, and first memory means coupled to said control means for receiving and storing a program instruction set for directing the operation of said control means in accordance with a predetermined delivery schedule whereby said predetermined incremental volume of fluid is pumped from said at least one reservoir means during a predetermined time interval such that the total of the incremental volumes pumped during the predetermined time interval is equal to a volume specified in the medication delivery schedule.

2. An ambulatory medication delivery system as defined in claim 1 further comprising:

means defining a first communication unit for coupling said portable infusion means thereto and for providing a first bi-directional information transfer link between said portable infusion means and said first communication unit means to receive and transmit information to and from said portable infusion means, and said first communication unit means further including memory means for storing information received from said portable infusion means whereby said stored information is uniquely identified and associated one-for-one with each one of a number of different portable infusion means for subsequent selection and retrieval.

3. An ambulatory medication delivery system as defined in claim 2 wherein said first bi-directional information transfer link provided between said first communication unit means and said portable infusion means comprises a wireless communication transmission path means for transmitting information to and receiving information from said first communication unit means and said portable infusion means, respectively.

4. An ambulatory medication delivery system as defined in claim 2 further comprising means defining a host computer for selectively communicating with at least one of any of a number of different ones of said first communication unit means to transmit information to and receive information from said at least one first communication unit means, said host computer means further having memory means for storing at least one of a number of different medication delivery schedule program instruction sets for selective retrieval to program a portable infusion means whereby a desired medication delivery schedule program instruction set is transferred to said first memory means of said portable infusion means to cause said portable infusion means to deliver fluid to the patient in accordance with the desired medication delivery schedule.

5. An ambulatory medication delivery system as defined in claim 4 further comprising modem means coupled to said first communication unit means for establishing a telephone dial-up connection link with said host computer means, said host computer means further including modem means for connection to said telephone link whereby information is transferred between said host computer means and said first communication unit means.

6. An ambulatory medication delivery system as defined in claim 1 wherein said portable infusion means further includes enclosure means for supporting internally said at least one reservoir means and said at least one controllable pump means and said control means, said portable infusion means further having alarm means coupled to said enclosure means and said control means for sensing and detecting an unauthorized opening of said enclosure means and for causing said control means to shutoff said pump means in response to said sensing and detecting of an unauthorized opening, said control means further having means for determining and recording information indicating an unauthorized opening and the time of the unauthorized opening for subsequent access and retrieval.

7. An ambulatory medication delivery system as defined in claim 6 further including a power source comprising a battery pack for powering said portable infusion means, said battery pack being supported internally within said enclosure means.

8. An ambulatory medication delivery system as defined in claim 1 further comprising:

means defining a second communication unit for coupling said portable infusion means thereto and for providing a second bi-directional information transfer link between said portable infusion means and said second communication unit means to receive and transmit information to and from said portable infusion means.

9. An ambulatory medication delivery system as defined in claim 8 wherein said second bi-directional information transfer link provided between said second communication unit means and said portable infusion means comprises a wireless communication transmission path means for transmitting information to and receiving information from said second communication unit means and said portable infusion means, respectively.

10. An ambulatory medication delivery system as defined in claim 8 further comprising:

said second communication unit means further including memory means for storing information received from said portable infusion means for subsequent retrieval, and means for providing a third bi-directional information transfer link between said first communication unit means and said second communication unit means whereby information received and stored in said second communication unit memory means is transferred to said first communication unit means.

11. An ambulatory medication delivery system as defined in claim 8 further comprising means defining a host computer for selectively communicating with at least one of any of a number of different ones of said second communication unit means to transmit information to and receive information from said at least one second communication unit means, said host computer means further having memory means for storing at least one of a number of different medication delivery schedule program instruction sets for selective retrieval to program a portable infusion means whereby a desired medication delivery schedule program instruction set is transferred to said second memory means of said portable infusion means to cause said portable infusion means to deliver fluid to the patient in accordance with the desired medication delivery schedule.

12. An ambulatory medication delivery system as defined in claim 11 wherein said second communication unit means further includes modem means for establishing a telephone dial-up connection link with said host computer means, said host computer means further including modem means for connection to said telephone link whereby information is transferred between said host computer means and said second communication unit means.

13. An ambulatory medication delivery system as defined in claim 12 wherein said second communication unit means further includes: a microprocessor, signal unit means coupled to said microprocessor for receiving electrical signals representative of a patient's vital signs whereby information representative of said vital signs is transferred to said host computer via the telephone dial-up link for monitoring by said host computer.

14. An ambulatory medication delivery system as defined in claim 1 further comprising:
 means defining a host computer for selectively communicating with at least one of any of a number of different ones of said portable infusion means to transmit information thereto;
 radio transmission beeper means coupled to said host computer means for receiving information from the host computer and for transforming the information to a format for transmission to said selected portable infusion means;
 antenna means coupled to said radio transmission beeper means for transmitting said formatted information;
 means defining a third communication unit for receiving said transmitted formatted information and converting said received transmitted information to electrical signals representative of the transmitted information, said third communication unit means further having means for providing an information transfer link between said third communication unit means and said portable infusion means to transfer said information to said portable infusion means;
 said host computer means further having memory means for storing at least one of a number of different medication delivery schedule program instruction sets for selective retrieval to program a portable infusion means whereby a desired medication delivery schedule program instruction set is transferred to said second memory means of said portable infusion means to cause said portable infusion means to deliver fluid to the patient in accordance with the desired medication delivery schedule.

15. An ambulatory medication delivery system as defined in claim 1 wherein said at least one controllable pump means further comprises:
 first piston stop means located within said main housing bore in the region nearest said inlet end portion;
 second piston stop means located within said main housing bore in the region of said main housing nearest said outlet end portion, said second piston stop means comprising axially facing sealing means carried by said fluid outlet and disposed coaxially within said main housing bore;
 said shutoff valve means further comprising an axially facing, radial flat surface for contacting said axially facing sealing means to prevent communication between said main housing bore and said fluid outlet, said shutoff valve means further having an interior cavity defined by circumferential walls having one end attached to said axially facing, radial flat surface and its opposite end outwardly open and in communication with said piston means axial bore, said circumferential walls having apertures therethrough to provide communication between the interior of the cavity and said main housing bore whereby said interior of said cavity is in communication with said fluid outlet when said piston means is moved in a direction toward said input end portion;
 a first one-way valve means located within said main housing bore at said output end portion and having an open operative state for allowing fluid flow in a direction from said inlet end portion to said outlet end portion and a closed operative state preventing fluid flow in a direction from said outlet end portion to said inlet end portion;
 a second one-way valve means located at and carried by said piston in the region of said shutoff valve means and having an open operative state for allowing fluid flow in a first direction from said inlet end portion to said outlet end portion and into said interior cavity of said shutoff valve means and having a closed operative state preventing fluid flow in a direction from said outlet end portion to said inlet end portion.

16. An ambulatory medication delivery system as defined in claim 15 wherein said spring means is disposed axially within said main housing bore between said piston means and said first piston stop means.

17. An ambulatory medication delivery system as defined in claim 16 wherein said spring means is selected from a group of elongated springs, each elongated spring in said group having a spring length and characteristic to generate a spring force to move said piston with a desired force to produce a predetermined desired pumping pressure.

18. An ambulatory medication delivery system as defined in claim 16 wherein second piston moving means comprises a first electromagnet coaxially surrounding said piston means and said main housing body for generating a magnetic field to cause said piston to move in a direction from said outlet end portion toward said inlet end portion when the intensity of said magnetic field is sufficient to overcome the bias force produced by said spring and for sensing and detecting said piston contacting said first piston stop means at the end of an intake stroke.

19. An ambulatory medication delivery system as defined in claim 18 wherein said controllable pump means further includes a second electromagnet coaxially surrounding said main housing body in the region of said variable volume dumping chamber for sensing and detecting said piston contacting said second piston stop means at the end of a pumping stroke.

20. An ambulatory medication delivery system as defined in claim 19 wherein said first and second electromagnets are coupled to control means whereby said first electromagnet is energized to produce a magnetic field for a predetermined time interval T1 during which time said piston is moved on its intake stroke from said outlet end portion to said second piston stop means and said second electromagnet is energized to produce a magnetic field for a predetermined time interval T1+T2 during which said piston is moved on its pumping stroke from said inlet end portion to said first piston stop means, said control means being responsive to a change in magnetic field at the end of the intake stroke and a change of magnetic field at the end of the pumping stroke, said control means detecting an alarm condition when said intake stroke is not completed within said time interval T1 and when said pumping stroke is not completed within said time interval T1+T2.

21. An ambulatory medication delivery system as defined in claim 21 further comprising said axially elongated housing body and said piston means being removable as an assembled unit from a said at least one controllable pump means and directly replaceable with another assembled unit.

22. An ambulatory medication delivery system as defined in claim 1 wherein said controllable pump means further includes means releaseably and sealingly connected to said inlet end portion for coupling a supply of fluid to said fluid inlet means.

23. An ambulatory medication delivery system as defined in claim 1 wherein said means for coupling said pump fluid outlet to said tube communication means is releaseably and sealingly connected to said outlet end portion to deliver fluid to a patient when said controllable pump means is activated.

24. An ambulatory medication delivery system comprising:

an ambulatory pumping unit carried by a patient and having a cyclically operated linear motor pumping means and a control computer connected to the pumping means for pumping a predetermined incremental volume of medication fluid into the patient in each cycle of operation, the pumping unit also having a memory for receiving and storing a program instruction set for directing the operation of the pumping means in accordance with a predetermined delivery schedule;

a full-authority remote clinician communication unit for establishing a communication link with the ambulatory pumping unit and sending new program instruction sets to the memory of the ambulatory pumping unit to change the predetermined delivery schedule; and a patient communication unit for establishing a communication link between the ambulatory pumping unit and the full-authority clinician unit, and providing patient vital sign data, the communication link with the ambulatory pumping unit and the clinician unit being established at the initiative of the patient and independently of the link between the clinician communication unit and the ambulatory pumping unit for sending new instruction sets.

25. An ambulatory medication delivery system as defined in claim 24 wherein the ambulatory pumping unit and the patient communication units have separate power supplies.

26. An ambulatory medication delivery system as defined in claim 24 wherein the patient communication unit has no capability of communicating new instruction sets to the ambulatory pumping unit.

* * * * *